United States Patent [19]

Ogata et al.

[11] 4,162,270
[45] Jul. 24, 1979

[54] PROCESS FOR PRODUCING 4,4′-DIHYDROXYDIPHENYLSULFONE OF HIGH PURITY

[75] Inventors: Eiji Ogata; Koji Ono; Shoji Nakagaki, all of Wakayama, Japan

[73] Assignee: Konishi Chemical Industry Co., Ltd., Wakayama, Japan

[21] Appl. No.: 896,611

[22] Filed: Apr. 14, 1978

Related U.S. Application Data

[63] Continuation-in-part of Ser. No. 771,546, Feb. 24, 1977, abandoned.

[51] Int. Cl.$^2$ ............................................. C07C 147/10
[52] U.S. Cl. .................................. 260/607 AR; 203/28
[58] Field of Search .................... 260/607 AR, 607 A; 203/28

[56] References Cited

U.S. PATENT DOCUMENTS

| | | | |
|---|---|---|---|
| 2,833,828 | 5/1958 | Sauls | 260/607 AR |
| 3,297,766 | 1/1967 | Bradley et al. | 260/607 AR |
| 3,318,956 | 5/1967 | Mausner | 260/607 AR |
| 3,383,421 | 5/1968 | Fox et al. | 260/607 AR |
| 3,855,312 | 12/1974 | Horner | 260/607 AR |
| 4,012,451 | 3/1977 | Enoki et al. | 260/607 AR |
| 4,016,210 | 4/1977 | Horner et al. | 260/607 AR |

*Primary Examiner*—Donald G. Daus
*Assistant Examiner*—M. C. Eakin
*Attorney, Agent, or Firm*—Armstrong, Nikaido, Marmelstein & Kubovcik

[57] ABSTRACT

In a process for producing 4,4′-dihydroxydiphenylsulfone by reacting phenol with sulfuric acid in the presence of a solvent, an improvement which comprises using at least a member selected from the group consisting of chlorobenzene, dichlorobenzene, trichlorobenzene, chlorotoluene, diethylbenzene, xylene, decalin, tetralin and tetrachloroethane as the solvent and removing said solvent progressively and finally substantially completely from the mixture while maintaining the reaction mixture at a temperature of about 160° to about 200° C. to effect precipitation of 4,4′-dihydroxydiphenylsulfone and isomerization of 2,4′-dihydroxydiphenylsulfone to 4,4′-dihydroxydiphenylsulfone.

3 Claims, No Drawings

PROCESS FOR PRODUCING 4,4'-DIHYDROXYDIPHENYLSULFONE OF HIGH PURITY

This application is a continuation-in-part of our co-pending application Ser. No. 771,546 filed on Feb. 24, 1977, now abandoned.

This invention relates to a process for producing 4,4'-dihydroxydiphenylsulfone of high purity, and more particularly to a process for producing 4,4'-dihydroxydiphenylsulfone from phenol and sulfuric acid.

It is known to prepare 4,4'-dihydroxydiphenylsulfone from phenol and sulfuric acid. This process yields 4,4'-dihydroxydiphenylsulfone along with large quantities of 2,4'-dihydroxydiphenylsulfone as an isomer by-product. However, extreme difficulty is encountered in separating the 4,4'-dihydroxydiphenylsulfone directly from the resulting reaction mixture.

In recent years, 4,4'-dihydroxydiphenylsulfone has found many uses and attracted much attention in the field of chemical industry relating to fibers and resins. For these uses, 4,4'-dihydroxydiphenylsulfone must have a high purity, with its 2,4'-dihydroxydiphenylsulfone content usually limited to not more than about 1% by weight. Despite such requirement, the reaction product of the known process contains as much as 20 to 30% by weight of 2,4'-dihydroxydiphenylsulfone and is in no way usable as it is. Although various attempts have been made to separate pure 4,4'-dihydroxydiphenylsulfone from the reaction product, i.e., from the mixture of 4,4'-dihydroxydiphenylsulfone and 2,4'-dihydroxydiphenylsulfone, it is commercially very disadvantageous to react phenol with sulfuric acid and subsequently separate the desired product from the resulting reaction mixture because of the additional cumbersome step of separation which must usually be followed by another step of purification.

An object of this invention is to provide a process for producing 4,4'-dihydroxydiphenylsulfone of high purity from phenol and sulfuric acid without necessitating any separation or purification step.

Another object of this invention is to provide a process for producing 4,4'-dihydroxydiphenylsulfone containing not more than 1% by weight of 2,4'-dihydroxydiphenylsulfone without resorting to any separation or purification step.

These and other objects of this invention will become apparent from the following description.

By way of illustration, the formation of 4,4'-dihydroxydiphenylsulfone takes place in the steps in accordance with the following equations:

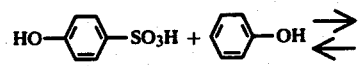

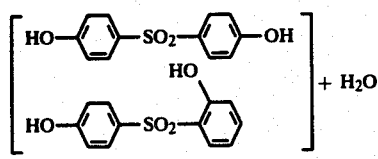

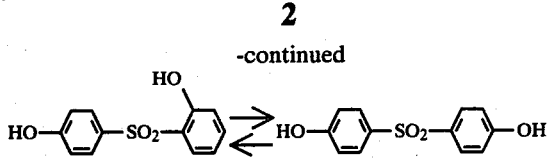

Hereinafter, the reaction of the equations (1) and (2) is referred to as "dehydration reaction" and the reaction of the equation (3) is referred to as "isomerization".

In producing 4,4'-dihydroxydiphenylsulfone by reacting phenol with sulfuric acid in the presence of a solvent by refluxing an azeotropic mixture of the solvent and water produced by the reaction, separating off the water alone and returning the solvent to the reaction mixture in the course of the reaction to provide a reaction mixture containing 4,4'-dihydroxydiphenylsulfone and 2,4'-dihydroxydiphenylsulfone as an isomer by-product, the present invention is characterized in that at least a member selected from the group consisting of chlorobenzene, dichlorobenzene, trichlorobenzene, chlorotoluene, diethylbenzene, xylene, decalin, tetralin and tetrachloroethane is used as the solvent in an amount of about 0.1 to about 5 times that of phenol in terms of weight, and said solvent is progressively and finally substantially completely removed from the reaction mixture while maintaining the reaction mixture at a temperature of about 160° to about 200° C. throughout the solvent removal to effect precipitation of 4,4'-dihydroxydiphenylsulfone and isomerization of 2,4'-dihydroxydiphenylsulfone to 4,4'-dihydroxydiphenylsulfone.

Our research has revealed the following. When phenol is reacted with sulfuric acid in the presence of a solvent, 4,4'-dihydroxydiphenylsulfone and 2,4'-dihydroxydiphenylsulfone are contained in a liquid phase in the ratio of about 73 ~ about 76% by weight of the former to about 24 ~ about 27% by weight of the latter. The former has a melting point of 250° C., and the latter a melting point of 186° C. When the solvent is progressively removed by distillation at a temperature of about 160° to about 200° C., the 2,4'-dihydroxydiphenylsulfone formed by the reaction of phenol and sulfuric acid dissolves into the remaining solvent or, stated more strictly, melts to a liquid state, forming a liquid mixture with the solvent, whereas 4,4'-dihydroxydiphenylsulfone alone precipitates from the solvent after having dissolved therein to saturation. The precipitate of 4,4'-dihydroxydiphenylsulfone produced by removal of a solvent reduces the ratio thereof relative to the by-product in the liquid phase, thus permitting 2,4'-dihydroxydiphenylsulfone to change into 4,4'-dihydroxydiphenylsulfone by isomerization according to the above equation (3) so as to achieve the aforesaid ratio of about 73 ~ about 76:about 24 ~ about 27 (by weight). The resulting 4,4'-dihydroxydiphenylsulfone similarly precipitates, consequently failing to maintain the relative ratio. At the same time, the removal of the solvent promotes the precipitate of 4,4'-dihydroxydiphenylsulfone and accordingly the isomerization of 2,4'-dihydroxydiphenylsulfone into 4,4'-dihydroxydiphenylsulfone proceeds during the removal of the solvent. During the process of the isomerization, most of 2,4'-dihydroxydiphenylsulfone is changed into 4,4'-dihydroxydiphenylsulfone with the eventual result that the remaining 2,4'-dihydroxydiphenylsulfone is left only as an impurity of very small quantity when the solvent is finally removed. The reaction mixture, when finally distilled off to substantially completely remove the solvent, yields 4,4'-dihydroxydiphenylsulfone which contains 2,4'-dihydroxydiphenylsulfone in an amount of not more than 1% by weight based on the 4,4'-dihydroxydiphenylsulfone. This invention has been accomplished based on the novel finding described above.

2,4'-dihydroxydiphenylsulfone, despite it's melting point of 185° C., melts to a liquid state at 160° C. for the following reason. The reaction between phenol and sulfuric acid is an equilibrium one in which phenol and sulfuric acid are not always totally converted to 4,4'- and 2,4'-dihydroxydiphenylsulfones, but the starting materials and intermediate products such as phenol sulfonic acid are present in the system. The presence of such substances renders 2,4'-dihydroxydiphenylsulfone meltable at 160° C.

When 4,4'-dihydroxydiphenylsulfone is prepared according to the present invention, it is critical to remove the solvent while maintaining the reaction mixture at a temperature of about 160° to about 200° C.

When this solvent removal is effected at a temperature not higher than 160° C., the isomerization of 2,4'-dihydroxydiphenylsulfone into 4,4'-dihydroxydiphenylsulfone tends to proceed in a low velocity, and even when the solvent is removed to give the precipitate of 4,4'-dihydroxydiphenylsulfone, the isomerization reaction hardly proceeds, thus yielding a product containing large quantity of 2,4'-dihydroxydiphenylsulfone. Conversely, when the solvent is removed at a temperature not less than 200° C., the 4,4'-dihydroxydiphenylsulfone precipitated tends to melt and the 4,4'-dihydroxydiphenylsulfone melted is isomerized into 2,4'-dihydroxydiphenylsulfone to recover the aforesaid isomer ratio of about 73 ~ about 76:about 24 ~ about 27.

The reaction of this invention requires the presence of a solvent. The absence of a solvent decreases the amount of the water removed, the water being produced by the reaction of phenol with sulfuric acid and inhibits the above reaction. Moreover, the absence of a solvent reduces the amount of 4,4'-dihydroxydiphenylsulfone precipitated since 4,4'-dihydroxydiphenylsulfone is highly soluble with phenol. The amount of solvent to be used, although not strictly limited, is about 0.1 to about 5 times, preferably about 0.3 to about 3 times that of phenol by weight.

Useful solvents are a wide variety of those inert under the reaction conditions, especially those in which 2,4'-dihydroxydiphenylsulfone is more soluble than 4,4'-dihydroxydiphenylsulfone, preferably with a great solubility difference therebetween. Examples of most preferable solvents are chlorobenzene, dichlorobenzene, trichlorobenzene, chlorotoluene, diethylbenzene, xylene and like aromatic hydrocarbon solvents, decalin, tetralin, tetrachloroethane, etc.

In the present invention it is critical to remove the solvent completely from the reaction mixture. However, the time for removal of the solvent is not limited insofar as the removal of the solvent is conducted at a temperature of about 160° to about 200° C. For example, the solvent may be removed after the dehydration reaction is substantially completed, or the solvent may be gradually removed during the progress of the dehydration reaction. However, it is not preferable in the present invention to remove all of the solvent before the completion of the dehydration reaction in order to minimize the content of isomeric 2,4'-dihydroxydiphenylsulfone.

The amounts of phenol and sulfuric acid are the same as in the conventional process. Generally phenol is used in at least two times the amount of sulfuric acid in terms of mole.

To practice the process of this invention, phenol, sulfuric acid and a solvent are placed into a reactor, and the mixture is heated at a temperature of about 130° ~ about 220° C. The water resulting from the progress of the reaction is removed by refluxing a mixture of the solvent and water, separating off the water alone in the course of reflux and returning the solvent to the reactor. The solvent to be returned can be partly drawn off from the reaction mixture. When the dehydration reaction has been almost completed, the solvent is substantially completely removed from the system. The solvent is readily removable by distillation suitably reducing the internal pressure of the reactor. The dry solid residue obtained is dissolved in an aqueous solution of alkali, and the solution is treated with active carbon to remove small amounts of colored impurities and then neutralized with an inorganic acid such as $H_2SO_4$, HCl, etc. to obtain 4,4'-dihydroxydiphenylsulfone crystals, separating by filtration from the filtrate which contains phenol sulfonic acid as a by-product.

In this way, when the solvent is substantially completely removed from the reaction mixture, the present process gives 4,4'-dihydroxydiphenylsulfone containing not more than about 1% by weight of 2,4'-dihydroxydiphenylsulfone generally in yields of at least 90%.

Thus according to this invention, 4,4'-dihydroxydiphenylsulfone of significantly high purity can be prepared from phenol and sulfuric acid without necessitating any further step for the separation of the isomer by-product.

This invention will be described below with reference to examples.

EXAMPLE 1

A mixture of 290 g (3.09 moles) of phenol, 146 g of 98% sulfuric acid and 150 g of o-dichlorobenzene is heated with stirring. When the temperature of the reaction system reaches about 150° C., the mixture begins to boil, giving off an azeotropic mixture of water and o-dichlorobenzene, which is condensed and separated into two phases, i.e., water and o-dichlorobenzene. The o-dichlorobenzene is continuously returned to the reaction mixture. With continuous heating, when the amount of the aqueous phase reaches 52 ml, the temperature of reaction mixture is about 180° C. Subsequently o-dichlorobenzene containing small amounts of water and phenol is completely distilled off over a period of 3 hours by reducing a pressure of the reaction system to produce the dried reaction mixture in a solid state, while adjusting the temperature to 175° to 185° C. When analyzed by gas chromatography, the dried reaction mixture is found to contain 0.9% by weight of 2,4'-dihydroxydiphenylsulfone based on 4,4'-dihydroxydiphenylsulfone present therein (hereinafter referred to as isomer content). A solution of 62 g of sodium hydroxide in 3.5 l of water is added to the residue, 5 g of active carbon is added to the solution, the mixture is filtered and the filtrate is neutralized with sulfuric acid. The resulting crystals are filtered off, then washed with water and dried, giving 332 g of 4,4'-dihydroxydiphenylsulfone, melting at 248° C., in a yield of 91.2% based on the sulfuric acid starting material. When analyzed by gas chromatography, the product is found to contain 0.8% of isomer content.

EXAMPLE 2

The same procedure as in Example 1 is repeated except that trichlorobenzene is used in place of o-dichlorobenzene, whereby 4,4'-dihydroxydiphenylsulfone, melting at 248.2° C., is obtained in a yield of 92.0% based on the sulfuric acid starting material. When analyzed in the same manner as in Example 1, the isomer content is found to be 1.0% in the dried mixture, and 0.7% in the product.

EXAMPLE 3

A mixture of 290 g (3.09 moles) of phenol, 146 g (1.46 moles) of 98% sulfuric acid and 90 g of tetrachloroethane is heated with stirring. When the temperature of the reaction system reaches about 140° C., the mixture begins to boil, giving off an azeotropic mixture of water and tetrachloroethane, which is condensed and separated into two phases, i.e., water and tetrachloroethane. The tetrachloroethane is continuously returned to the reaction mixture. With continuous heating, when the amount of the aqueous phase reaches 45 ml, the temperature of reaction mixture is about 160° C. Subsequently tetrachloroethane containing small amounts of water and phenol is completely distilled off over a period of 4 hours by reducing a pressure of the reaction system to produce the dried reaction mixture in a solid state, while adjusting the temperature to 160° to 170° C. A solution of 62 g of sodium hydroxide in 3.5 l of water is added to the residue, 5 g of active carbon is added to the solution, the mixture is filtered and the filtrate is neutralized with sulfuric acid. The resulting cyrstals are filtered off, then washed with water and dried, giving 332 g of 4,4'-dihydroxydiphenylsulfone, melting at 248° C., in a yield of 91.2% based on the sulfuric acid starting material. When analyzed by gas chromatography, the isomer content is found to be 1.2% in the dried reaction mixture and 0.8% in the product.

EXAMPLE 4

A mixture of 343 g (3.69 moles) of phenol, 146 g (1.46 moles) of 98% sulfuric acid and 300 g of o-dichlorobenzene is heated with stirring. When the temperature of the reaction system reaches about 140° C., the mixture begins to boil, giving off an azeotropic mixture of water and o-dichlorobenzene, which is condensed and separated into two phases, i.e., water and o-dichlorobenzene. The o-dichlorobenzene is continuously returned to the reaction mixture. With continuous heating, when the amount of the aqueous phase reaches 55 ml, the temperature of reaction mixture is about 184° C. Subsequently o-dichlorobenzene containing small amounts of water and phenol is completely distilled off over a period of 3 hours by reducing a pressure of the reaction system to produce the dried reaction mixture in a solid state, while adjusting the temperature to 180° to 190° C. A solution of 62 g of sodium hydroxide in 3.5 l of water is added to the residue, 5 g of active carbon is added to the solution, the mixture is filtered and the filtrate is neutralized with sulfuric acid. The resulting crystals are filtered off, then washed with water and dried, giving 338 g of 4,4'-dihydroxydiphenylsulfone, melting at 248.5° C., in a yield of 92.6% based on the sulfuric acid starting material. When analyzed by gas chromatography, the isomer content is found to be 0.6% in the dried reaction mixture and 0.5% in the product.

COMPARISON EXAMPLE 1

The same procedure as in Example 1 is repeated except that 150 g of phenol is used in place of 150 g of o-dichlorobenzene, whereby 4,4'-dihydroxydiphenylsulfone, melting at 240.0° C., is obtained in a yield of 89.5% based on the sulfuric acid starting material. When analyzed by gas chromatography, the reaction mixture, after the dehydration reaction is substantially completed, is found to contain 25.0% by weight of 2,4'-dihydroxydiphenylsulfone based on 4,4'-dihydroxydiphenylsulfone present therein. The isomer content is found to be 13% in the dried mixture and 12% in the product.

What we claim is:

1. A process for producing 4,4'-dihydroxydiphenyl sulphone of extremely high purity which comprises the steps of reacting phenol with sulfuric acid in a solvent inert to the reactants under refluxing while separating off the water produced by the reaction until at least about 80% of the water to be produced is removed from the reaction system, and then removing said solvent progressively and finally substantially completely from the reaction system while maintaining the reaction mixture at a temperature of 160° to 200° C. throughout the solvent removal to effect isomerization of 2,4'-dihydroxydiphenylsulfone to 4,4'-dihydroxydiphenyl sulfone.

2. A process as defined in claim 1 wherein the solvent is gradually removed during and after the reaction.

3. A process as defined in claim 1 wherein the solvent is removed after the reaction is substantially completed.

* * * * *